United States Patent
Yang et al.

(10) Patent No.: US 10,426,810 B2
(45) Date of Patent: Oct. 1, 2019

(54) TANGERINE PEEL EXTRACT AND ITS PREPARATION AND APPLICATION

(75) Inventors: Yiting Yang, Guangdong (CN); Hujie Luo, Guangdong (CN); Wei Sun, Guangdong (CN); Haiyan Ou, Guangdong (CN); Shuo Liu, Guangdong (CN); Chungwah Ma, Guangdong (CN)

(73) Assignee: Infinitus (China) Company Ltd., Jinagmen, GD (CN)

( * ) Notice: Subject to any disclaimer, the term of this patent is extended or adjusted under 35 U.S.C. 154(b) by 855 days.

(21) Appl. No.: 13/355,530

(22) Filed: Jan. 21, 2012

(65) Prior Publication Data

US 2012/0189732 A1     Jul. 26, 2012

(30) Foreign Application Priority Data

Jan. 21, 2011 (CN) .......................... 2011 1 0023489

(51) Int. Cl.
| | |
|---|---|
| *A61K 36/752* | (2006.01) |
| *A23L 19/00* | (2016.01) |
| *A23L 27/12* | (2016.01) |
| *A23L 33/00* | (2016.01) |
| *A23L 33/105* | (2016.01) |

(52) U.S. Cl.
CPC ............ *A61K 36/752* (2013.01); *A23L 19/07* (2016.08); *A23L 27/13* (2016.08); *A23L 33/105* (2016.08); *A23L 33/30* (2016.08); *A61K 2236/13* (2013.01)

(58) Field of Classification Search
CPC ............ A61K 2236/31; A61K 2300/00; A61K 36/753; A61K 8/97
See application file for complete search history.

(56) References Cited

PUBLICATIONS

Santiago et al. (2010) J. Pharm. Sci & Res. vol. 2 (11), 752-758.*
Asnaashari et al. (2010) Phytother. Res. 24: 1893-1897.*
Mira et al. (1999) J. Supercritical Fluids 14: pp. 95-104.*
Reverchon (1997) J. Supercritical Fluids 10, pp. 1-37.*
Tu et al. (2002) Flavour Fragr. J. 17: 169-174.*
Wenqiang et al. (2007) Food Chemistry 101: 1558-1564.*
Porta et al. (1997) J. Essent. Oil Res., 9, 515-522.*
Revilla et al. (1998) J. Agric. Food Chem. 46: 4592-4597.*

* cited by examiner

*Primary Examiner* — Russell G Fiebig
(74) *Attorney, Agent, or Firm* — George G. Wang; Bei & Ocean

(57) ABSTRACT

This invention disclosed a tangerine peel extract, which is obtained from tangerine peels as raw materials through supercritical $CO_2$ extraction. Such tangerine peel extract contains a large amount of flavonoid and terpenoid compositions that can effectively regulate the functions of the spleen and stomach; and has the effect of weight loss. This invention also declares the preparation method of the above mentioned tangerine peel extract, which is simple in technique and highly efficient in extraction. This invention also further declares the application of the above mentioned tangerine peel extract in preparing the healthcare food, which possesses the function of weight loss.

1 Claim, No Drawings

TANGERINE PEEL EXTRACT AND ITS PREPARATION AND APPLICATION

FIELD OF THE INVENTION

The present invention relates to the technical field of healthcare food. In particular, it relates to the preparation and application of tangerine peel extract.

BACKGROUND OF THE INVENTIO

There are reportedly over 90 million obese and about 200 million overweight individuals in the current Chinese population. Weight loss products accounted for 60 billion Chinese Yuan in the aggregate market in 2010. The population fraction accounted by the obese and overweight will increase as living standards improve, and the market will continue to expand. From years of clinical observation and research of Traditional Chinese Medicine ("TCM" hereinafter), the main reasons for obesity have been suggested as follows: 1) Obese patients have 'Spleen Deficiency, often accompanied by the symptoms of phlegmatic hygrosis and deficiency of vital energy. The spleen is the foundation of "acquired constitution" (i.e., the human body) and a source of generating "Qi" and "Blood". Lowered-level functioning of the spleen results in production of "Dampness", which leads to production of "Phlegm". When Qi is obstructed, the Phlegm is unable to be transported, leading to the tendency of "Phlegm-Dampness". According to Su Wen's "Strange Disease Theory" described in the book of Huang Di Nei Jing, most obese people have the tendency of Phlegm-Dampness. According to the theory, Qi, Blood, Jing and "Body Fluid" are unable to be transported and transformed due to Spleen and Qi Deficiency, leading to obesity. 2) Most obese patients have accumulation of "Heat", which accumulates primarily in the "Stomach". According to "Treatise on the spleen and stomach" (i.e., according to TCM theories), when Heat accumulates in the spleen and stomach, food is digested too quickly leading to constant hunger. Therefore, it is difficult for obese patients to curb their appetite, making weight control even more difficult. To prevent and regulate these relevant symptoms of obese patients, it is necessary to begin with the regulation and improvement of the functions of the Spleen and Stomach.

TCM emphasizes the prevention of a disease before its onset and stresses dietary treatment. Hence, raw materials chosen for invigorating the Spleen and improving the Stomach are edible TCM materials that have been utilized for thousands of years and processed by appropriate extraction techniques to obtain the components effective in weight loss.

SUMMARY OF THE INVENTION

The first object of the present invention is to provide an extract of tangerine peel comprising the flavonoid- and terpenoid-containing components, capable of regulating the functions of the Spleen and Stomach and have weight loss properties.

The second object of the present invention is to provide a preparation method of producing the tangerine peel extract, which is simple and highly efficient.

The third object of the present invention is to provide a health-care use of the tangerine peel extract.

The first object of the present invention is achieved by the following technique: the tangerine peel extract is prepared by supercritical $CO_2$ extraction.

The second object of the present invention is achieved as follows: the tangerine peel extract is prepared in a process where the raw material is the tangerine peel which is extracted with supercritical $CO_2$ to afford an extract.

In this technical solution, the supercritical $CO_2$ extraction conducted for duration of 1-3 hours at the pressure of 10-40 MPa and the temperature of 30-50° C. The flow velocity of $CO_2$ is 1-100 L/h, and the supercritical $CO_2$ extraction is followed by separations via the separating tank to prepare the extract.

The tangerine peel should be pulverized before extraction, and the pulverized tangerine peel has a particle size of 10-80 mesh.

The third object of the present invention is achieved by the following technical solution: the use of the aforesaid tangerine peel extract in the preparation of healthcare food with a weight loss effect. The tangerine peel extract processed by supercritical $CO_2$ extraction, after having been supplemented with the additives such as glycerin, sodium carboxymethylcellulose, can be consumed as a healthcare food having a weight loss effect. Alternatively, the tangerine peel extract can be a major component and supplemented with pharmaceutically acceptable additives to manufacture healthcare food, wherein the pharmaceutically acceptable additives are one or more selected from the group consisting of mannitol, sorbitol, sodium metabisulphite, sodium hydrosulfite, Vitamin C, disodium EDTA, sodium bicarbonate, calcium bicarbonate, calcium sulfate, sodium chloride, sodium lactate, xylitol, maltose, fructose, dextran, ferrous sulfate, starch, dextrin, sucrose, lactose, silicon derivatives, cellulose and derivatives hereof, sodium carboxymethyl starch, gelatin, agar, polyethylene pyrrole, glycerin, paraffin wax, TWEEN-80, polyethylene glycol (PEG), compressible starch, surfactants, cyclodextrin and derivatives hereof, talcum powder and magnesium stearate. The aforesaid healthcare food can be formulated into tablets, gel capsules, oral liquid, granules, pill, etc.

The present invention has the following advantages:

1. The tangerine peel extract is both food and medicine. Since it contains a large amount of flavonoids and terpenoids components, it regulates the functions of Spleen and Stomach effectively, and functions as invigorating Spleen and resolving Dampness, thus has an effect of weight loss.

2. The tangerine peel extract, processed by the extraction technology in the present invention, sufficiently retains and enriches the effective components having an effect of invigorating Spleen and tonifying Stomach, rendering said effective components to reduce weight by reducing energy intake and energy utilization ratio, by regulating the ability of pancreatic β cells to secret insulin so that to regulate sugar metabolisms, and by increasing the catabolism of cholesterol.

The present invention will be further illustrated by the following embodiments and the results of pharmacodynamical data.

DETAILED DESCRIPTION OF PARTICULAR EMBODIMENTS OF THE INVENTION

The following specific examples are listed to illustrate the present invention. It is necessary to point out that the following examples are only for the purpose of further illustration, but not deemed to restrict the scope of present invention. Some non-substantive changes and adjustment based on the present invention made by others shall still fall within the protection scope of the present invention.

Part I: The Tangerine Peel Extract and the Preparation Process Hereof

EXAMPLE 1

The tangerine peel extract provided in this example is prepared by the following process: 200 g of tangerine peel are pulverized into 80 mesh, then extracted in the supercritical $CO_2$ extraction device for 1 hour at the pressure of 35 MPa and temperature of 50° C., with a $CO_2$ flow velocity of 80 L/h. Finally, the extract is obtained from the separating tank.

EXAMPLE 2

The tangerine peel extract provided in this example is prepared by the following process: 100 g of tangerine peel are pulverized into 50 mesh, then extracted in the supercritical $CO_2$ extraction device for 2 hours at the pressure of 25 MPa and temperature of 40° C., with a $CO_2$ flow velocity of 20 L/h. Finally, the extract is obtained from the separating tank.

EXAMPLE 3

The tangerine peel extract provided in this example is prepared by the following process: 20 g of tangerine peel are pulverized into 10 mesh, then extracted in the supercritical $CO_2$ extraction device for 3 hours at the pressure of 15 MPa and temperature of 30° C., with a $CO_2$ flow velocity of 50 L/h. Finally, the extract is obtained from the separating tank.

EXAMPLE 4

The tangerine peel extract prepared in Example 1 is supplemented with appropriate amounts of glycerin, 2% (w/w) of sodium carboxymethylcellulose as required making a liquid product. Other conventional additives can also be used to make another conventional dosage form. The dosage is 10 g daily as calculated equivalent to the raw material (taking once each day).

EXAMPLE 5

The tangerine peel extract prepared in Example 2 is supplemented with appropriate amounts of glycerin, 2% (w/w) of sodium carboxymethylcellulose as required to make a liquid product. Other conventional additives can also be used to make another conventional dosage form. The dosage is 10 g daily as calculated equivalent to the raw material (taking once each day).

EXAMPLE 6

The tangerine peel extract prepared in Example 3 is supplemented with appropriate amounts of glycerin, 2% (w/w) of sodium carboxymethylcellulose as required to make a liquid product. Other conventional additives can also be used to make another conventional dosage form. The dosage is 10 g daily as calculated equivalent to the raw material (taking once each day).

Part II: The Efficacy Trials of the Tangerine Peel Extract for Reducing Weight

1. Trial Institution

The College of Veterinary Medicine at HUAZHONG Agricultural University

2. Experimental Purpose

Study the efficacy for reducing weight of the supercritical $CO_2$ extract of the present invention.

3. Materials, Grouping, Dosage and Administration Methods 3.1 Test Materials:

(1) The extract prepared in Example 4 is administered in a dosage of 10 g once-daily, calculated as the equivalent to the raw material.

(2) Experimental animals: SPF SD male rats, body weight ranging over 180-200 g. Qualification certificate No. for the SD rats: Shanghai SLAC Laboratory Animals Co., Ltd., SCXK (Shanghai) 2003-0003.

(3) Major devices and reagents used in the trials:

I. Olympus Automatic Biochemical Analyzer (made in Japan);

II. BIOTEK Microplate Reader;

III. KUBOTA KR-20000T refrigerated high-speed centrifuge (made in Japan);

IV. EPPendorf 5415R centrifuge;

V. Sigma 1-14 centrifuge;

VI. Onetouch blood glucose meter and Onetouch blood glucose accessories, (manufactured by Johnson & Johnson);

VII. HDL assay kit: manufactured by Zhongsheng BeiKong Biotechnology Co., Ltd.

3.2 Test Groups:

Three groups are assigned randomly by weight: I. normal control group; II. model control group; III. supercritical extract group (administered with the extract prepared in Example 4), each group consisting of 12 animals.

3.3 Test Dosage:

Samples are calculated as the equivalent to the raw material, the recommended dosage for human body is 10 g/60 kg/d, i.e., 167 mg/kg/d. calculated as 10 folds of the recommended dosage for human body, the equivalent dosage in rats is 1670 mg/kg/d.

3.4 Administration Method:

SPF SD male rats are randomly assigned into three groups: normal control group, obesity model control group, and supercritical extract group (namely test group). The rats in normal control group are fed with basal diet, while the rats in obesity model control group and test group are fed with high-fat diet. The feeding time for making the models is 45 days. After the models have been successfully made, normal control group and obesity model group are fed with distilled water via gastric tube daily, while the test group is fed with the sample of supercritical extract via gastric tube daily. The effects of the supercritical extract on the relevant indicators are assessed from the statistical analysis of the following data. The trial lasts 45 days.

4. Data Processing:

All the experimental data are processed and represented as mean±SD ($\bar{x}$±s), the data from two groups are compared by t test. All data are analyzed by statistical analysis software SPSS13.0. $P<0.05$ indicates a statistically significant difference.

5. The Test Procedure and Results:

5.1 The Effect of the Supercritical Extract on Lee's Index and Body Weight

TABLE 1

The effect of supercritical extract on body weight (g)

| Groups | Mean ± SD | Significance |
| --- | --- | --- |
| Normal control group | 454.50 ± 46.99 | ** |
| Obesity model control group | 519.38 ± 38.10 | |
| Supercritical extract test group | 488.80 ± 25.61 | ** |

Note:
The normal control group and supercritical extract test group are compared with the obesity model control group, respectively.
"NS" means p < 0.05,
"*" means p < 0.05,
"**" means p < 0.01, and
"***" means p < 0.001, the same as below.

It is seen from Table 1 that, the weight of normal control group is lower than that of obesity model control group significantly, and the weight of supercritical extract test group is also lower than that of obesity model control group significantly. Thus, it demonstrates that the supercritical extract has a weight loss effect.

TABLE 2

The effect of supercritical extract on Lee's index

| Groups | Mean ± SD | Significance |
| --- | --- | --- |
| Normal control group | 26.01 ± 0.77 | *** |
| Obesity model control group | 27.23 ± 0.43 | |
| Supercritical extract test group | 26.63 ± 0.43 | ** |

As seen from Table 2, the Lee's index of normal control group is lower than that of obesity model control group significantly. Thus, it demonstrates that the supercritical extract can regulate the obese constitution or tendency of obese rats very effectively.

5.2 The Effect of Supercritical Extract on the Visceral Fat Index

TABLE 3

The effect of supercritical extract on the visceral fat index of rats

| Groups | Mean ± SD | Significance |
| --- | --- | --- |
| Normal control group | 2.97 ± 0.42 | *** |
| Obesity model control group | 4.98 ± 0.90 | |
| Supercritical extract test group | 4.18 ± 0.53 | * |

As seen from Table 3, the visceral fat index of obesity model control group is higher than that of normal control group significantly. In comparison to the obesity model control group, the supercritical extract test group has a significantly reduced deposition of visceral fat.

5.3 The Effect of Supercritical Extract on Glucose Tolerance

TABLE 4

The effect of supercritical extract on glucose tolerance (mmol/L/h)

| Groups | Mean ± SD | Significance |
| --- | --- | --- |
| Normal control group | 11.40 ± 0.76 | *** |
| Obesity model control group | 13.10 ± 0.69 | |
| Supercritical extract test group | 11.08 ± 0.93 | *** |

As seen from Table 4, the glucose tolerance of normal control group is significantly lower than that of obesity model control group. The result shows that the glucose tolerance of the obesity model control group is deficient, indicating that the rats in obesity model control group have abnormal sugar metabolism. Thus, it demonstrates that the supercritical extract can significantly regulate the deficient glucose tolerance caused by obesity.

5.4 The Effect of the Supercritical Extract on Fasting Plasma Glucose (FPG)

TABLE 5

The effect of supercritical extract on FPG (mmol/L)

| Groups | Mean ± SD | Significance |
| --- | --- | --- |
| Normal control group | 5.10 ± 0.19 | *** |
| Obesity model control group | 6.76 ± 0.47 | |
| Supercritical extract test group | 5.98 ± 0.78 | ** |

As seen from Table 5, the FPG of obesity model control group is significantly higher than the FPG of normal control group, which indicates that the FPG of obesity model control group is deficient. The FPG of supercritical extract test group is lower than the FPG of obesity model control group significantly. The result demonstrates that the supercritical extract has a significant beneficial effect on the abnormal FPG caused by obesity.

5.5 The Effect of Supercritical Extract on the Serum HDL of Rats

TABLE 6

The effect of supercritical extract on the serum HDL of rats (mmol/L)

| Groups | Mean ± SD | Significance |
| --- | --- | --- |
| Normal control group | 0.73 ± 0.10 | *** |
| Obesity model control group | 0.58 ± 0.07 | |
| Supercritical extract test group | 0.67 ± 0.05 | ** |

As seen from Table 6, the serum HDL of obesity model control group is significantly lower than that of normal control group. Thus, it demonstrates that the supercritical extract can improve the serum HDL effectively.

5.6 The Effect of Supercritical Extract on the Serum AST/ALT of Rats

TABLE 7

The effect of supercritical extract on the serum AST/ALT

| Groups | Mean ± SD | Significance |
| --- | --- | --- |
| Normal control group | 3.11 ± 0.31 | *** |
| Obesity model control group | 4.27 ± 0.34 | |
| Supercritical extract test group | 3.91 ± 0.21 | NS |

As seen from Table 7, the AST/ALT value of obesity model control group is significantly higher than that of normal control group. The result indicates that obesity seriously has damaged the liver function of obesity model control group. Although the supercritical extract does not show statistically significant protection of the injured liver function caused by obesity, it demonstrates a tendency of protecting the liver function.

6. Conclusion:

The aforesaid experimental results show that the supercritical $CO_2$ extract of tangerine peel has a weight loss effect.

What is claimed is:

1. A method of improving glucose tolerance in an obese person comprising administering an effective amount of a tangerine (*Citrus tangerine*) peel extract with an acceptable carrier;
   wherein said tangerine peel extract is free of D-limonene and is prepared by a process comprising
   (a) breaking 200 g long-term aged tangerine peel into pieces of 80 mesh;
   (b) extracting the pieces of tangerine peels for one hour with supercritical carbon dioxide as an extraction medium at a flow rate of 80 L/h, under a pressure of 35 MPa and at a temperature of 50° C.

* * * * *